United States Patent
Leeton

(10) Patent No.: US 10,618,858 B2
(45) Date of Patent: Apr. 14, 2020

(54) IONIC LIQUID REACTOR WITH HYDROCYCLONES

(71) Applicant: UOP LLC, Des Plaines, IL (US)

(72) Inventor: Eric Leeton, Corpus Christi, TX (US)

(73) Assignee: UOP, LLC, Des Plaines, IL (US)

( * ) Notice: Subject to any disclaimer, the term of this patent is extended or adjusted under 35 U.S.C. 154(b) by 0 days.

(21) Appl. No.: 15/217,918

(22) Filed: Jul. 22, 2016

(65) Prior Publication Data

US 2017/0022127 A1 Jan. 26, 2017

Related U.S. Application Data

(60) Provisional application No. 62/196,653, filed on Jul. 24, 2015.

(51) Int. Cl.
*C07C 2/60* (2006.01)

(52) U.S. Cl.
CPC .......... *C07C 2/60* (2013.01); *C07C 2531/02* (2013.01)

(58) Field of Classification Search
None
See application file for complete search history.

(56) References Cited

U.S. PATENT DOCUMENTS

| | | |
|---|---|---|
| 4,764,440 A | 8/1988 | Jones et al. |
| 5,104,840 A | 4/1992 | Chauvin et al. |
| 5,824,832 A | 10/1998 | Sherif et al. |
| 7,285,698 B2 * | 10/2007 | Liu .......................... C07C 2/58 585/709 |
| 7,951,889 B2 * | 5/2011 | Bergman ............ B01J 19/1806 422/129 |
| 8,067,656 B2 | 11/2011 | Luo et al. |
| 8,552,243 B2 | 10/2013 | Liu et al. |
| 8,569,561 B2 | 10/2013 | Liu et al. |
| 8,653,318 B2 | 2/2014 | Liu et al. |
| 2009/0171134 A1 * | 7/2009 | Luo .......................... C07C 2/60 585/14 |
| 2013/0345482 A1 * | 12/2013 | Martins ..................... C07C 2/56 585/722 |

FOREIGN PATENT DOCUMENTS

CN 1785940 A 6/2006

* cited by examiner

*Primary Examiner* — In Suk C Bullock
*Assistant Examiner* — Alyssa L Cepluch

(57) ABSTRACT

A method of alkylating a hydrocarbon stream including: providing a feed stream that includes hydrocarbons and ionic liquid catalyst; passing the feed stream through a low efficiency mixer to create a mixed stream, whereby the low efficiency mixer creates droplets within the feed stream that are primarily within a predetermined size range; passing the mixed stream and an olefin stream into a reactor; performing an alkylation reaction within the reactor, thereby forming a reacted stream; and separating the reacted stream into a settled ionic liquid catalyst stream and a hydrocarbon stream through the use of at least one hydrocyclone.

14 Claims, 1 Drawing Sheet

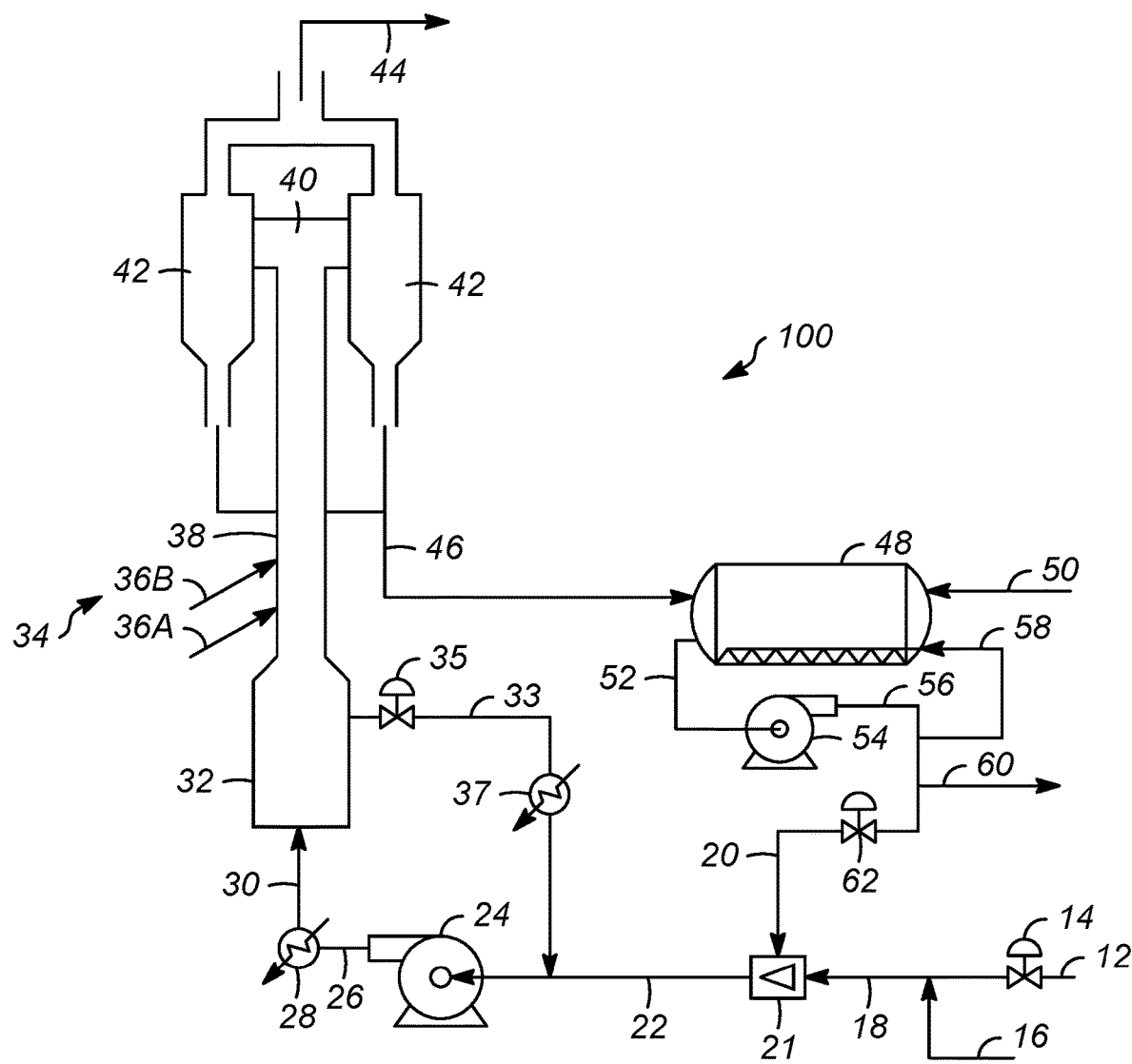

IONIC LIQUID REACTOR WITH HYDROCYCLONES

CROSS-REFERENCE TO RELATED APPLICATION

This application claims priority from Provisional Application No. 62/196,653 filed Jul. 24, 2015, the contents of which are hereby incorporated by reference.

BACKGROUND OF THE INVENTION

The present invention relates generally to processing hydrocarbons, and more particularly to processes and units using an ionic liquid catalyst, especially where the reactor of the unit includes one or more hydrocyclones.

There are a variety of different types of hydrocarbon conversion processes, with each one designed to obtain a particular resulting product (or products). One such process is alkylation.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls. Ionic liquids provide advantages over other catalysts, including being less corrosive than catalysts like hydrofluoric acid, and being non-volatile.

The alkylation of paraffins with olefins for the production of alkylate for gasolines can use a variety of catalysts. The choice of catalyst depends on the end product a producer desires. Ionic liquids are catalysts that can be used in a variety of catalytic reactions, including the alkylation of paraffins with olefins. Ionic liquids are primarily mixtures of salts which melt below room temperature, and will form liquid compositions at temperature below the individual melting points of the constituents.

Ionic liquids are essentially salts in a liquid state, and are described in U.S. Pat. Nos. 4,764,440, 5,104,840 and 5,824,832. The properties vary extensively for different ionic liquids, and the use of ionic liquids depends on the properties of a given ionic liquid. Depending on the organic cation of the ionic liquid and the anion, the ionic liquid can have very different properties.

The current ionic liquid reactor practice utilizes mixers within the mixing chamber of the reactor to create the desired droplet size and size distribution, and employs multiple reactors with inter-reactor exchangers. The mixers must run at relatively high revolutions-per-minute (rpm), which causes concern with shaft movement and potential complications with seals/packing. Given the unique nature and characteristics of the ionic liquid catalyst, there is also concern with material settling in the inter-reactor exchangers. Maintaining the proper disposition of the ionic liquid catalyst during the transition between reactors is also of concern.

The present invention provides an improved ionic liquid reactor unit that addresses these concerns.

BRIEF SUMMARY OF THE INVENTION

Briefly, embodiments of the ionic liquid reactor of the present invention include the use of one or more hydrocyclone(s) in combination with a low-efficiency pump and mixing chamber recycle line to control droplet size and size distribution within the mixing chamber of the reactor vessel. The proper sizing of the riser of the reactor and suitable flow rates through the riser will keep the ionic liquid catalyst from coalescing and settling. The reactor riser can be designed to provide the desired residence time for the reaction. The use of olefin feed injection nozzles at multiple elevations can provide more flexibility for residence time for the reaction, as well as reducing the likelihood of localized spots of a low ratio of isobutenes to oelfins.

Hydrocyclones have demonstrated the ability to provide effective separation in other areas. For example, in waste water service, hydrocyclones have demonstrated 75% recovery of droplets of 30 microns and smaller. The ionic liquid catalyst of the present invention is expected to be maintained with droplet size at or about 100 microns, or smaller. Further, the hydrocyclones as used in the present invention are believed to be capable of separating droplets smaller than 30 microns with efficiencies at times in excess of 90%. The use of hydrocyclones allows the effective removal of ionic liquid catalyst from the hydrocarbon stream, and thus provides effective control of the residence time.

As explained more fully below, embodiments of the present invention preferably include the present invention preferably a low efficiency pump in combination with a mixing chamber recycle line, which allows for the control of droplet size and size distribution. The RPM and recycle flow rate can be set based on the data provided by a monitoring system including high speed cameras provided in the mixing chamber of the reactor vessel. A standard centrifugal pump may create droplets that are too fine, and thus difficult to settle. The use of a pump with the properly designed impellor i.e., an impellor designed for mixing, would produce droplets with the desired characteristics. Riser sizing i.e., the length and diameter, should be set to provide the desired residence time. The use of multiple, mixed olefin feed nozzles adds more residence time flexibility, so that the unit and process can be used with different feed and ionic liquid catalyst combinations. The temperature in the reaction zone will impact selectivity, and therefore should be controlled. The ionic liquid catalyst/isobutane in the mixing chamber recirculation can be chilled to control the riser outlet temperature. Likewise, the recirculated ionic liquid catalyst/isobutane could also be cooled after it is mixed with the isobutane recycle from the fractionation section. Additionally, a cooling water jacket could be included in the mixing chamber and reactor riser for additional heat removal. Further certain alkylation reactors that could be used as part of the present invention remove heat from within the reactor, while other embodiments "pre-cools" the ionic liquid catalyst to control the riser outlet temperature. Cooling could also be applied to the riser outlet/hydrocyclone inlets. This would not only help to control the reaction temperatures, but the lower temperatures would make the ionic liquid catalyst more dense, and thus would facilitate separation within the hydrocyclone(s).

One aspect of the present invention relates to a method of alkylating a hydrocarbon stream including: providing a feed stream that includes hydrocarbons and ionic liquid catalyst;

passing the feed stream through a low efficiency mixer to create a mixed stream, whereby the low efficiency mixer creates droplets within the feed stream that are primarily within a predetermined size range; passing the mixed stream and an olefin stream into a reactor; performing an alkylation reaction within the reactor, thereby forming a reacted stream; and separating the reacted stream into a settled ionic liquid catalyst stream and a hydrocarbon stream through the use of at least one hydrocyclone.

Another aspect of the invention relates to a method of alkylating a hydrocarbon stream including: premixing a hydrocarbon feed stream and an ionic liquid stream within a pre-mixer to form a pre-mixed stream; passing the pre-mixed stream through a low efficiency mixer to create a mixed stream, whereby the low efficiency mixer creates droplets within the pre-mixed stream; passing the mixed stream into a reactor; providing an olefin stream to the reactor; performing an alkylation reaction within the reactor, thereby forming a reacted stream; and passing the reacted stream through at least one hydrocyclone to form a settled ionic liquid catalyst stream and a hydrocarbon stream.

Another aspect of the invention relates to an ionic liquid reactor unit including a reactor vessel including a mixing chamber and a riser section; at least one hydrocyclone, wherein the at least one hydrocyclone is configured and arranged to receive a reacted stream from a top portion of the riser; at least one olefin feed line for providing an olefin feed to the reactor vessel; a feed line for providing a feed to the mixing chamber of the reactor vessel, wherein the feed line provides a feed stream that includes hydrocarbons and ionic liquid catalyst to the mixing chamber of the reactor vessel; and a recycle line that directs a mixing chamber recycle stream out of the mixing chamber, through a low efficiency mixer, and then back into the mixing chamber.

BRIEF DESCRIPTION OF THE DRAWING

Preferred embodiments of the present invention are described herein with reference to the drawings wherein:

The FIGURE is a process flow diagram of the primary components of one example of an embodiment of the present invention.

DETAILED DESCRIPTION OF THE INVENTION

Ionic liquids, as used hereinafter, refer to the complex of mixtures where the ionic liquid comprises an organic cation and an anionic compound where the anionic compound is usually an inorganic anion.

The anionic component of the ionic liquid generally comprises a haloaluminate of the form $Al_nX_{3n+1}$, where n is from 1 to 5. The most common halogen, Ha, is chlorine, or Cl. The ionic liquid mixture can comprise a mix of the haloaluminates where n is 1 or 2, and include small amount of the haloaluminates with n equal to 3 or greater.

In the present invention, the ionic liquid is preferably a phosphonium based ionic liquid, and the present invention includes alkylation of paraffins using a phosphonium based ionic liquid, or other suitable ionic liquid. The process includes passing a paraffin having from 2 to 10 carbon atoms to an alkylation reactor, and in particular an isoparaffin having from 4 to 10 carbon atoms to the alkylation reactor. An olefin having from 2 to 10 carbon atoms is passed to the alkylation reactor. The olefin and isoparaffin are reacted in the presence of an ionic liquid catalyst and at reaction conditions to generate an alkylate. The ionic liquid catalyst is preferably a phosphonium based haloaluminate ionic liquid coupled with a Bronsted acid co-catalyst selected from the group consisting of HCl, HBr, HI and mixtures thereof.

Specific example of ionic liquids that could be used with the present invention include phosphonium based ionic liquids selected from the group consisting of trihexyl-tetradecyl phosphonium-$Al_2X_7$, tributyl-hexylphosphonium-$Al_2X_7$, tripropylhexylphosphonium-$Al_2X_7$, tributylmethylphosphonium-$Al_2X_7$, tributylpentylphos-phonium-$Al_2X_7$, tributylheptyl-phosphonium-$Al_2X_7$, tributyloctylphosphonium-$Al_2X_7$, tributylnonylphosphonium-$Al_2X_7$, tributyldecylphosphonium-$Al_2X_7$, tributylundecylphos-phonium-$Al_2X_7$, tributyldodecyl-phosphonium-$Al_2X_7$, tributyltetradecylphosphonium-$Al_2X_7$, and mixtures thereof X comprises a halogen ion selected from the group consisting of F, Cl, Br, I, and mixtures thereof. A preferred ionic liquid is tri-n-butyl-hexylphosphonium-$Al_2X_7$, where the preferred halogen, X, is selected from Cl, Br, I and mixtures thereof. Another preferred ionic liquid is tributylpentylphosphonium-$Al_2X_7$, wherein X comprises a halogen ion selected from the group consisting of Cl, Br, I and mixtures thereof. Another preferred ionic liquid is tributyloctylphosphonium-$Al_2X_7$, wherein X comprises a halogen ion selected from the group consisting of Cl, Br, I and mixtures thereof. In particular, the most common halogen, X, used is Cl.

The specific examples of ionic liquids in the present invention could include phosphonium based ionic liquids mixed with aluminum chloride. The acidity is preferably controlled to provide for suitable alkylation conditions. The ionic liquid is generally prepared to a full acid strength with balancing through the presence of a co-catalyst, such as a Bronsted acid. HCl or any Bronsted acid may be employed as co-catalyst to enhance the activity of the catalyst by boosting the overall acidity of the ionic liquid-based catalyst.

Due to the low solubility of hydrocarbons in ionic liquids, olefins-isoparaffins alkylation, like most reactions in ionic liquids, is generally biphasic and takes place at the interface in the liquid phase. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range 1 to 100, for example, advantageously in the range 2 to 50, preferably in the range 2 to 20.

In a semi-batch or continuous system, the isoparaffin is introduced first then the olefin, or a mixture of isoparaffin and olefin. The catalyst is measured in the reactor with respect to the amount of olefins, with a catalyst to olefin weight ratio between 0.1 and 10, and preferably between 0.2 and 5, and more preferably between 0.5 and 2. Vigorous stirring is desirable to ensure good contact between the reactants and the catalyst. The heat generated by the reaction can be eliminated using any of the means known to the skilled person. At the reactor outlet, the hydrocarbon phase is separated from the ionic liquid phase by hydrocyclone(s). Then the hydrocarbons are further processed.

Typical alkylation conditions may include a catalyst volume in the reactor of from 1 vol % to 50 vol % and an isobutane to olefin molar ratio of from 2 to 20. The paraffin used in the alkylation process preferably comprises an isoparaffin having from 4 to 8 carbon atoms, and more preferably having from 4 to 5 carbon atoms. The olefin used in the alkylation process preferably has from 3 to 8 carbon atoms, and more preferably from 3 to 5 carbon atoms.

Turning now to the FIGURE, one example of an embodiment of the present process and ionic liquid reactor unit 100 is shown and will be described. The relevant portion of the present process starts with a hydrocarbon feed stream 12, such as a feed stream including 90% isobutane ($iC_4$), which may be the result of other refinery or chemical manufacturing units. The feed stream 12 passes through a valve 14, and may be combined with a make-up liquid stream 16, such as hydrochloric acid (HCl) stream, or a stream of another suitable acid or liquid, to form a combined stream 18. The combined stream 18 passes into a pre-mixer 21, where it is mixed with an ionic liquid catalyst stream 20, which will be described in more detail below. The pre-mixer 21 could be any desired type of fixed or static mechanical mixer. For example, it could be a perforated pipe, a helical inline mixer, or a static mixer.

The pre-mixed stream 22 exiting the pre-mixer 21 is combined with a mixing chamber recycle stream 33 (described below) and the combined stream is passed through a "low efficiency" final mixer 24, which may consist of a "low efficiency" pump with a variable rpm, thereby enabling for the ability to adjust the rpm to obtain the desired droplet size and size distribution. A "low efficiency" pump is utilized because a standard centrifugal pump may create droplets that are too fine, and thus would not settle out from the mixture or emulsion in the desired manner in the subsequent process steps. In this context, the term "low efficiency" means a pump or mixer in which more energy is utilized for breaking droplets than the energy used for conveying the liquid through the pump or mixer. Suitable low efficiency pumps include, but are not limited to, high shear pumps, rotor-stator pumps, and cavitation reactor pumps.

In the present invention, the desired droplet size and size distribution, or more accurately, the Sauter Mean Diameter (or SMD) is dependent upon the particular ionic liquid catalyst used and on other process conditions. One of the objectives of the present process involves obtaining a particular average droplet size while maintaining a relatively narrow range of droplet sizes. Thus, the present process enables for controlling both droplet size and size distribution.

After exiting the low efficiency final mixer 24, final-mixed stream 26 preferably passes through a cooling device 28 prior to passing through line 30 and into a mixing chamber 32 of a reactor 34. The cooling device 28 may be any desired cooling device, such as a shell and tube heat exchanger or a plate heat exchanger, which could be air cooled, water cooled, or that uses another cooling medium, such as a glycol mix. The cooling device 28 may cool the stream 26 to a desired temperature that is above the reactor temperature, at the reactor temperature, or below the reactor temperature, depending upon what is need to control the reaction within the reactor 34. For example, the temperature at the reactor outlet may be 70° F., and depending upon what is needed to control the reaction, the stream 26 may be cooled to any desired temperature, such as 90° F., 70° F. or even 50° F. If desired, the mixing chamber 32 may include a cooling jacket (not shown) to provide additional cooling.

One or more olefin feed lines 36A, 36B enter into the mixing chamber 32 to provide an olefin feed or mixed olefin feed (consisting of olefin feed mixed with any required make-up isobutene) to the mixing chamber 32. The olefin feed preferably has molecules with from 2 to 8 carbon atoms, but more preferably this feed has molecules with from 3 to 5 carbon atoms. Preferably, the nozzles associated with the olefin feed lines 36A, 36B are staged at different elevations to help control residence time and to minimize the likelihood of localized spots of high olefin concentration. Example of such nozzles include, but are not limited to, internal ring nozzles and spray nozzles. Although only two olefin feed lines are shown at different elevations, more than two lines may also be provided at more than two different elevations.

As briefly mentioned above, the present invention also preferably includes the mixing chamber recycle line 33, which is associated with a valve 35 and a second cooling device 37. The second cooling device 37 may be any desired cooling device, such as a shell and tube heat exchanger or a plate heat exchanger, which could be air cooled, water cooled, or that uses another cooling medium, such as a glycol mix. After the recycle stream has been cooled in the second cooling device 37, it joins the pre-mixed stream 22, and the combined stream passes through the low efficiency final mixer 24 and the first cooling device 28 before entering the mixing chamber 32. The speed (RPM) of the low efficiency final mixer 24 and the flow rate of the recycle line 33 can be adjusted, via a control means (including a computer processor), based on data received from a system that monitors the conditions within the mixing chamber 32, such as the droplet size and size distribution, which could be monitored by a monitoring system such as smart online particle analysis technology products and systems offered by SOPAT GmbH of Berlin, Germany, so that the desired droplet size range and size distribution can be maintained.

Within the mixing chamber 32 and the riser 38 of the reactor 34, an alkylation reaction is performed, and thus this portion of the reactor of this embodiment will be termed the alkylation zone. However, it should be noted that other configurations for the alkylation zone are also contemplated. Alkylation reaction temperatures within the contemplation of the present invention are in the range of from about 5° C. to about 150° C., and are more preferably within the range of about 10° C. to about 27° C. Lower temperatures favor alkylation reaction of isoparaffins with olefins over competing olefin side reactions such as polymerization. However, overall reaction rates decrease with decreasing temperatures. Temperatures within the given range, and preferably in the range of from about 30° C. to about 130° C. provide good selectivity for alkylation of isoparaffins with olefins at commercially attractive reaction rates.

Reaction pressures contemplated in the present invention may range from pressures sufficient to maintain reactants in the liquid phase to about 15 atmospheres of pressure. Reactant hydrocarbons may be normally gaseous at alkylation reaction temperatures, thus, reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst composition of the present invention generally should be sufficient to provide for essentially complete conversion of olefin reactants in the alkylation zone. Preferably, the contact time is in the range of from about 0.05 minute to about 60 minutes. In the alkylation process of the present invention, employing isoparaffins to olefin molar ratios in the range of about 2:1 to about 25:1, wherein the alkylation reaction mixture comprises about 40 to 90 volume percent catalyst phase and about 10 to 60 volume percent hydrocarbon phase, and wherein good contact of olefins with isoparaffins is maintained in the reaction zone, essentially complete conversion of olefins may be obtained at olefin space velocities in the range of about 0.1 to about 200 volumes olefin per volume catalyst per hour (v/v/hr.) Optimum space velocities will depend upon the type of isoparaffins and olefin reactants utilized, the particular compositions of alkylation catalyst, and the alkylation reaction conditions. Consequently, the preferred contact times are sufficient for providing an olefin space velocity in the range of about 0.1 to about 200 v/v/hr. and allowing essentially complete conversion of the olefin reactant in the alkylation zone.

In continuous operations, for example, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence or other general means in the flow system.

After sufficient residence time, the reacted stream moves from the top 40 of the riser 38 and enters one or more hydrocyclones 42 (preferably between 2 and 15, or more, hydrocyclones). Within the hydrocyclones 42, the ionic liquid catalyst is separated from the hydrocarbon stream. The hydrocarbon stream can be passed through hydrocyclone effluent line 44, and can be directed to other components for further processing, such as to a settler, coalescer or a fractionator.

The ionic liquid catalyst that is settled out of the composition by the action of the hydrocyclones 42 passes, via settled ionic liquid stream line 46, into a storage vessel, such as a surge drum 48. A line 50 provides a feed of make-up activated ionic liquid to maintain the desired level of the composition within surge drum 48. An output line 52 from the surge drum 48 passes the ionic liquid catalyst stream into a pump 54 (which could be any desired pump, such as a standard refinery service type pump, which could be centrifugal, positive displacement, canned drive, magnetic drive, motor driven, etc.) and then through line 56. The stream within line 56 can be branched off to a recirculation line 58, which recirculates the ionic liquid catalyst stream back into the surge drum 48 to prevent settling of the contents within the drum 48. The stream within line 56 can also be branched off to a slipstream line 60, by closing valve 62, which slipstream line 60 passes the ionic liquid catalyst stream to other components for regeneration, which may be accomplished by any desired method. The ionic liquid catalyst stream within line 56 that is not directed through either line 58 or line 60 passes through the valve 62, and then into the pre-mixer 21 via the line 21.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims. Various features of the invention are set forth in the appended claims.

Specific Embodiments

While the following is described in conjunction with specific embodiments, it will be understood that this description is intended to illustrate and not limit the scope of the preceding description and the appended claims.

A first embodiment of the invention is a method of alkylating a hydrocarbon stream comprising providing a feed stream that includes hydrocarbons and ionic liquid catalyst; passing the feed stream through a low efficiency mixer to create a mixed stream, whereby the low efficiency mixer creates droplets within the feed stream that are primarily within a predetermined size range; passing the mixed stream and an olefin stream into a reactor; performing an alkylation reaction within the reactor, thereby forming a reacted stream; and separating the reacted stream into a settled ionic liquid catalyst stream and a hydrocarbon stream through the use of at least one hydrocyclone. An embodiment of the invention is one, any or all of prior embodiments in this paragraph up through the first embodiment in this paragraph, further comprising passing a recycle stream from a mixing chamber of the reactor through a mixing chamber recycle line and into the low efficiency mixer prior to passing the recycle stream back into the mixing chamber of the reactor. An embodiment of the invention is one, any or all of prior embodiments in this paragraph up through the first embodiment in this paragraph, further comprising cooling the recycle stream prior to entering the low efficiency mixer. An embodiment of the invention is one, any or all of prior embodiments in this paragraph up through the first embodiment in this paragraph, further comprising obtaining data on the droplet size of the ionic liquid catalyst within the mixing chamber, and using the data to regulate the speed of the low efficiency mixer and the flow rate of the recycle stream. An embodiment of the invention is one, any or all of prior embodiments in this paragraph up through the first embodiment in this paragraph, further comprising cooling the mixed stream after passing through the low efficiency mixer but prior to passing into the reactor. An embodiment of the invention is one, any or all of prior embodiments in this paragraph up through the first embodiment in this paragraph, further comprising passing the settled ionic liquid catalyst stream from the at least one hydrocyclone to a surge drum; providing a make-up ionic liquid stream to the surge drum; and combining a stream from the surge drum with the feed stream within a pre-mixer. An embodiment of the invention is one, any or all of prior embodiments in this paragraph up through the first embodiment in this paragraph, wherein the ionic liquid catalyst stream includes a phosphonium based ionic liquid catalyst. An embodiment of the invention is one, any or all of prior embodiments in this paragraph up through the first embodiment in this paragraph, wherein the feed stream includes isobutane. An embodiment of the invention is one, any or all of prior embodiments in this paragraph up through the first embodiment in this paragraph, wherein the step of passing an olefin stream into the reactor comprises passing multiple olefin streams into a riser of the reactor and multiple different elevations. An embodiment of the invention is one, any or all of prior embodiments in this paragraph up through the first embodiment in this paragraph, wherein the olefin stream includes molecules having from 3 to 8 carbon atoms.

A second embodiment of the invention is a method of alkylating a hydrocarbon stream comprising premixing a hydrocarbon feed stream and an ionic liquid stream within a pre-mixer to form a pre-mixed stream; passing the pre-mixed stream through a low efficiency mixer to create a mixed stream, whereby the low efficiency mixer creates droplets within the pre-mixed stream; passing the mixed stream into a reactor; providing an olefin stream to the reactor; performing an alkylation reaction within the reactor, thereby forming a reacted stream; and passing the reacted stream through at least one hydrocyclone to form a settled ionic liquid catalyst stream and a hydrocarbon stream. An embodiment of the invention is one, any or all of prior embodiments in this paragraph up through the second embodiment in this paragraph, further comprising passing a recycle stream from a mixing chamber of the reactor through a mixing chamber recycle line and into the low efficiency mixer prior to passing the recycle stream back into the mixing chamber of the reactor. An embodiment of the invention is one, any or all of prior embodiments in this paragraph up through the second embodiment in this paragraph, further comprising cooling at least one of the following: (i) the recycle stream; (ii) pre-mixed stream; (iii) the reacted stream prior to being passed through the at least one hydrocyclone; and (iv) the mixing chamber of the reactor. An embodiment of the invention is one, any or all of prior embodiments in this paragraph up through the second embodiment in this paragraph, further comprising passing the settled ionic liquid catalyst stream from the at least one hydrocyclone to a surge drum; providing a make-up ionic liquid stream to the surge drum; and combining a stream from the surge drum with the feed stream within a pre-mixer. An embodiment of the invention is one, any or all of prior embodiments in this paragraph up through the second embodiment in this paragraph, further comprising obtaining data on the droplet size of the ionic liquid catalyst within the mixing chamber, and using the data to regulate the speed of the low efficiency mixer and the flow rate of the recycle stream. An embodiment of the invention is one, any or all of prior embodiments in this paragraph up through the second embodiment in this paragraph, wherein the ionic liquid catalyst stream includes a phosphonium based ionic liquid catalyst.

A third embodiment of the invention is an apparatus comprising a reactor vessel including a mixing chamber and a riser section; at least one hydrocyclone, wherein the at least one hydrocyclone is configured and arranged to receive a reacted stream from a top portion of the riser; at least one olefin feed line for providing an olefin feed to the reactor vessel; a feed line for providing a feed to the mixing chamber of the reactor vessel, wherein the feed line provides a feed stream that includes hydrocarbons and ionic liquid catalyst to the mixing chamber of the reactor vessel; and a recycle line that directs a mixing chamber recycle stream out of the mixing chamber, through a low efficiency mixer, and then back into the mixing chamber. An embodiment of the invention is one, any or all of prior embodiments in this paragraph up through the third embodiment in this paragraph, wherein the recycle line is in communication with the feed line upstream of the low efficiency mixer, whereby the feed stream and the mixing chamber recycle stream are mixed within the low efficiency mixer to form a mixed stream prior to entering the mixing chamber of the reactor vessel. An embodiment of the invention is one, any or all of prior embodiments in this paragraph up through the third embodiment in this paragraph, further comprising means for obtaining data on the droplet size of the ionic liquid catalyst within the mixing chamber, and control means for using the data to regulate the speed of the low efficiency mixer and the flow rate of the recycle stream. An embodiment of the invention is one, any or all of prior embodiments in this paragraph up through the third embodiment in this paragraph, comprising means for cooling at least one of the mixing chamber and/or the area of the reactor between the riser and the entrance to the at least one hydrocyclone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A method of alkylating a hydrocarbon stream comprising:
   providing a reactor and a feed stream that includes paraffinic or aromatic hydrocarbons and ionic liquid catalyst;
   combining the feed stream with a mixing chamber recycle stream from a mixing chamber of the reactor to form a combined stream;
   passing the combined stream through a low efficiency mixer to create a mixed stream, wherein said low efficiency mixer includes a pump which creates droplets within said combined stream that are within a predetermined size range;
   passing the mixed stream and an olefin stream into the reactor, wherein the reactor has a top and a bottom, and wherein the mixed stream and the olefin stream enter the reactor at the bottom of the reactor;
   performing an alkylation reaction within the reactor, thereby forming a reacted stream; and
   separating the reacted stream into a settled ionic liquid catalyst stream and a hydrocarbon stream through the use of at least one hydrocyclone, wherein the hydrocarbon stream exits the reactor at the top of the reactor.

2. The method according to claim 1, further comprising cooling the recycle stream prior to entering the low efficiency mixer.

3. The method according to claim 1, further comprising measuring droplet size of the ionic liquid catalyst within the mixing chamber, and regulating the speed of the low efficiency mixer and the flow rate of the recycle stream based on the droplet size measured in the previous step.

4. The method according to claim 1, further comprising cooling the mixed stream after passing through the low efficiency mixer but prior to passing into the reactor.

5. The method according to claim 1, further comprising:
   passing the settled ionic liquid catalyst stream from the at least one hydrocyclone to a surge drum;
   providing a make-up ionic liquid stream to the surge drum; and
   combining a stream from the surge drum with the feed stream within a pre-mixer.

6. The method according to claim 1, wherein the ionic liquid catalyst stream includes a phosphonium based ionic liquid catalyst.

7. The method according to claim 1, wherein the feed stream includes isobutane.

8. The method according to claim 1, wherein the step of passing an olefin stream into the reactor comprises passing multiple olefin streams into a riser of the reactor at multiple different elevations.

9. The method according to claim 1, wherein the olefin stream includes molecules having from 3 to 8 carbon atoms.

10. The method according to claim 1, further comprising a step of pre-mixing the hydrocarbons and the ionic liquid catalyst within a pre-mixer to form the feed stream, wherein the pre-mixing step is performed before the step of combining the feed stream with a mixing chamber recycle stream.

11. The method according to claim 1, wherein the reactor is an upflow reactor.

12. The method according to claim 1, wherein the alkylation reaction is performed within the temperature range of about 5° C. to about 150° C.

13. The method according to claim 1, wherein the alkylation reaction is performed within the temperature range of about 30° C. to about 130° C.

14. The method according to claim 1, wherein the alkylation reaction is performed within the temperature range of about 10° C. to about 27° C.

* * * * *